United States Patent

Nomura

Patent Number: 5,859,937
Date of Patent: Jan. 12, 1999

[54] MINIMALLY INVASIVE SENSOR

[75] Inventor: Hiroshi Nomura, Shorewood, Minn.

[73] Assignee: NeoMecs Incorporated, Eden Prairie, Minn.

[21] Appl. No.: 832,941

[22] Filed: Apr. 4, 1997

[51] Int. Cl.⁶ ................................................. G02B 6/26
[52] U.S. Cl. .............................................. 385/12; 385/31
[58] Field of Search ................................ 385/12, 13, 31, 385/123, 15

[56] References Cited

U.S. PATENT DOCUMENTS

| | | | |
|---|---|---|---|
| 4,560,248 | 12/1985 | Cramp et al. | |
| 4,965,087 | 10/1990 | Wolfbeis et al. | |
| 5,114,864 | 5/1992 | Walt | 385/12 X |
| 5,244,636 | 9/1993 | Walt et al. | 385/12 X |
| 5,262,638 | 11/1993 | Egalon et al. | 385/12 X |
| 5,268,972 | 12/1993 | Tabacco et al. | 385/12 |
| 5,340,715 | 8/1994 | Slovacek et al. | 385/12 X |
| 5,349,181 | 9/1994 | Saini et al. | 385/12 X |
| 5,356,780 | 10/1994 | Robinson et al. | |
| 5,449,625 | 9/1995 | Kobayashi et al. | |
| 5,573,956 | 11/1996 | Hanning | 385/12 X |

FOREIGN PATENT DOCUMENTS 0256806  2/1988  European Pat. Off. .

OTHER PUBLICATIONS

Zhou et al., "Multichannel Evanescent Fluorescence Immunosensing Using Potassium and Sodium Ion–Exchanged Patterned Waveguides," Journal of Molecular Electronics, (1991 no month) 7, 135–149.

Primary Examiner—John D. Lee
Attorney, Agent, or Firm—Robert J. Petersen

[57] ABSTRACT

A minimally invasive sensing device, and method for its use, is disclosed which utilizes a light-conducting fiber having a localized textured site thereon, wherein a reagent is deposited. Interaction of the reagent with an analyte specific to the reagent produces a response, such as development of a colored product, which is detectable by means of a change in characteristics of a light beam transmittable through the fiber. By means of the textured site and its increased surface area, the sensitivity of the device is greatly enhanced, such that less than 5 microliters of a fluid is needed for an analysis. The sensor is particularly useful in blood glucose determinations, requiring smaller blood samples than flat strip devices.

16 Claims, 3 Drawing Sheets

MINIMALLY INVASIVE SENSOR

FIELD OF THE INVENTION

The present invention relates to a sensing device for determination of analytes in fluids, and more particularly to a minimally invasive sensing device for measuring glucose and other analytes in blood and biological fluids.

BACKGROUND OF THE INVENTION

The quantification of chemical and biochemical components in aqueous fluids, and particularly in biological fluids such as whole blood or urine and in biological fluid derivatives such as serum and plasma, is of ever increasing importance. Important applications exist in medical diagnosis and treatment and in the quantification of exposure to therapeutic drugs, intoxicants, hazardous chemicals and the like. These applications include the detection and quantification of an increasing variety of certain circulating antibodies, cancer-related metabolites, genetically derived chemical tracers, and hormones emitted during events such as pregnancy. In many instances, the amounts of materials being determined are minuscule—in the range of a microgram or less per deciliter—and readily analyzed only by means of complicated apparatus operated by skilled laboratory personnel. In such cases the results are generally not available for some hours or days after sampling. In other instances, there is often an emphasis on the ability of lay operators to perform analytical tests routinely, quickly and reproducibly in a nonlaboratory setting, with rapid or immediate information display.

One common medical test is the measurement of blood glucose levels by diabetics. Current teaching counsels diabetic patients to measure their blood glucose level from two to seven times a day, depending on the nature and severity of their individual cases. Based on the observed pattern in the measured blood glucose levels, the patient and physician together make adjustments in diet, exercise and insulin intake to better manage the disease. Clearly, this information should be available to the patient at the time of sampling.

This glucose determination typically entails the diabetic piercing the skin of his or her finger with a lance, followed by squeezing or expression of a blood droplet. The blood droplet is then transferred to a reagent pad or test strip. The amount of blood that is conveniently expressed from a finger prick is governed by the size and depth of penetration of the lance. Too small a nick results in an inadequately sized blood sample for the intended analysis. Pain is experienced in the lancing procedure, and the degree of pain is associated with the size and depth of penetration of the lance. Unfortunately, with current technology, a lancet size and required depth of penetration entails significant pain. The continual daily lancing of one's fingertips is a painful exercise necessarily tolerated by diabetics once or twice per day. More frequent testing than this, however, would bring on a serious problem of patient noncompliance, if required.

If the blood droplet size needed for a blood glucose determination can be significantly reduced, the pain associated with finger pricking can also be greatly reduced by reason of use of smaller lances and/or decreased depth of penetration into the flesh of the finger. There is indeed a need for an analytical sampling method, suitable for use by a diabetic patient, that requires less blood than current devices and methods, and which is therefore associated with less pain.

Determination of analytes in whole blood often involves colorimetric determinations utilizing color-generating reagents immobilized within reagent pads or porous media. The presence of red blood cells or other colored components in blood often interferes with such measurements. Exclusion of red blood cells and/or other blood cellular components has been practiced utilizing reagent pads with filterative or membranous layers specifically formed or laminated thereon. This tends to increase the complexity of such devices, as well as increasing the volume of blood that must be applied. Accordingly, in addition to the need for a smaller blood sample, a need also exists for a means of excluding cellular components of blood and body fluids without increasing the fluid sample size.

It is an object of this invention to provide a minimally invasive means of detecting and measuring analytes in both whole blood and other biological fluids. With regard to whole blood, it is a further object of this invention to provide a device capable of detecting and/or quantifying analytes without requiring a prior removal step for cellular blood components before blood contact with the device.

Another object of this invention to provide a device capable of detecting and/or quantifying a multiplicity of analytes in a single droplet of a bodily fluid.

Another object of this invention to provide a diabetic patient with a means of analyzing blood glucose concentrations in a manner that significantly reduces the pain associated with providing a sufficient blood sample for the glucose analysis.

These and other objects of the invention will be apparent to those skilled in this art from the following detailed description of preferred embodiments of the invention.

SUMMARY OF THE INVENTION

Novel sensors are now provided for diagnostic assays comprising light-conductive fibers having localized textured surface sites, with analyte-responsive reagents being deposited on the fibers at, on, or within the localized textured sites, these reagents producing observable physical or chemical responses upon being contacted with fluids containing the analytes they are responsive to, wherein the physical or chemical responses are observable and/or quantifiable by changes in light beam characteristics at one or more frequencies of light transmittable through the fiber. In particular, novel sensors in accordance with these attributes are provided, wherein penetration of certain colloidal or cellular components of the fluids into the textured surface sites is limited or prohibited by the structure of the texture.

Exemplary of this invention is an optical fiber having a site localized at a point along its length or at an end thereof, this site being textured into a cone field by means of ion beam sputtering, the spacing between projections of the cone field being sufficiently narrow as to limit or prohibit penetration of red blood cells into openings between the cone projections, an analyte-responsive reagent being deposited within the cone field, which generates a response detectable by light transmittable through the fiber. The response can be a colorimetric response to blood glucose occurring within the cone field due to reagents deposited thereat, on, or within, the presence of degree of the colorimetric response being measurable by frequency or amplitude changes in a light beam passed through the fiber.

Also exemplary of this invention is a similarly utilized optical fiber consisting of an organopolymeric composition, wherein a textured surface is produced by plasma etching at a localized site, the analyte-responsive reagent being deposited within the plasma-etched textured surface.

Also exemplary of this invention is a method of measuring an analyte in a fluid, such as for example glucose in whole blood, comprising bringing a fluid into contact with a light-conducting fiber having a localized textured surface site thereon, an analyte-responsive reagent being deposited within the textured site on the fiber, and allowing this reagent to interact with the analyte in the fluid, thereby producing an observable physical or chemical response detectable by light. As part of this method, a light beam of at least one frequency is transmitted through the fiber past the textured site, and is analyzed for changes in beam characteristics (such as frequency or amplitude) that are correlative with presence and concentration of the analyte in the fluid, distinguishable by means of the above-mentioned physical or chemical response by the reagent.

DETAILED DESCRIPTION OF THE INVENTION

Figure 1:
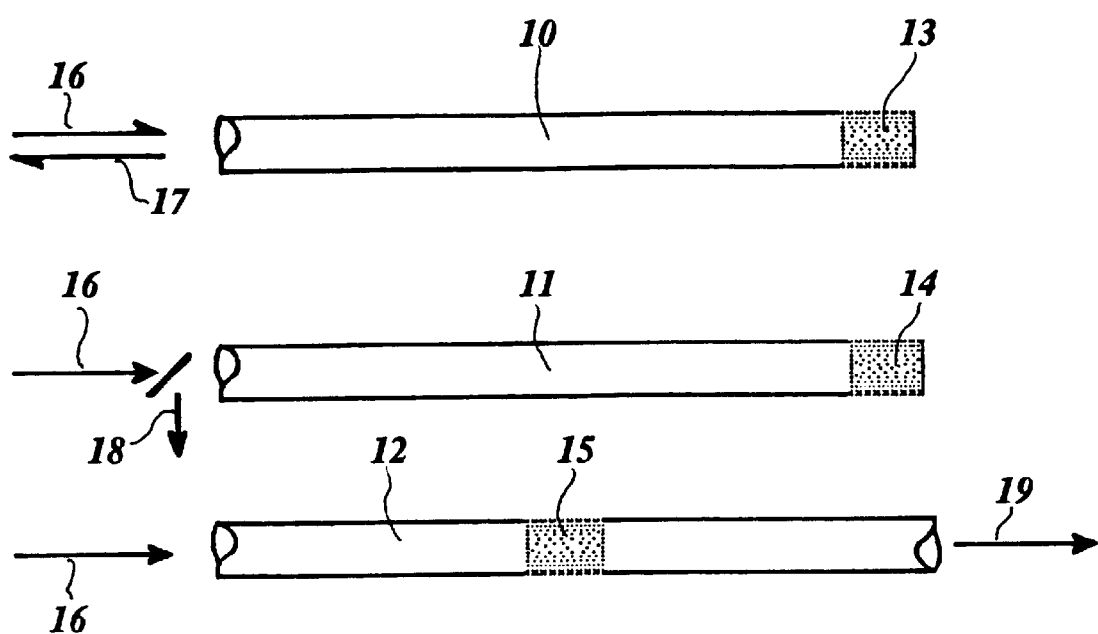
FIG. 1 is a schematic view of fibers with textured surface sites.

This invention will now be further described in connection with the accompanying drawings. FIG. 1 illustrates a general embodiment of the invention. Light-conductive fibers 10–12 are treated so as to have textured surfaces 13–15 at discrete, localized sites. Such a site may be located at any point along an individual fiber's length, such as site 15, but are preferably at or near fiber endings, such as sites 13–14. Fiber endings are obviously obtainable by pre-cutting fibers to predetermined lengths. The surface may be textured by one of several methods, including physical abrasion, chemical etching, sputtering or ablation by high energy beams, or deposition of dendritic-like structures thereon. At least one end of each of the light-conductive fibers 10–12 is placed adjacent to a light source for sending a beam of light 16 down the fiber length. At least one end of each of the fibers is also located adjacent to a device for measuring light beam characteristics of light 17–19 emanating from the fibers. This latter end may be either the same end as the initial end for beam entry, or may consist of a second end to the same fiber. When a single fiber ending is to be adjacent to both the light source and the device for measuring the light beam characteristics, light measurement is dependent upon reflection of the light beam 17,18 from some point along or at a second end of the fiber. The textured surface 13–15 is treated so as to contain an analyte-responsive reagent (not shown in FIG. 1). Alternatively, light may be captured within the fiber by transmittal through the textured site from an external source. In particular, a chemiluminescent or fluorescent reaction at the textured site resulting from reagent-analyte interactions can be advantageously utilized wherein a portion of the chemiluminescent or fluorescent light enters the fiber and is transmitted to a device such as a luminometer, located at one end of the fiber, for detection and quantitation.

Figure 2:
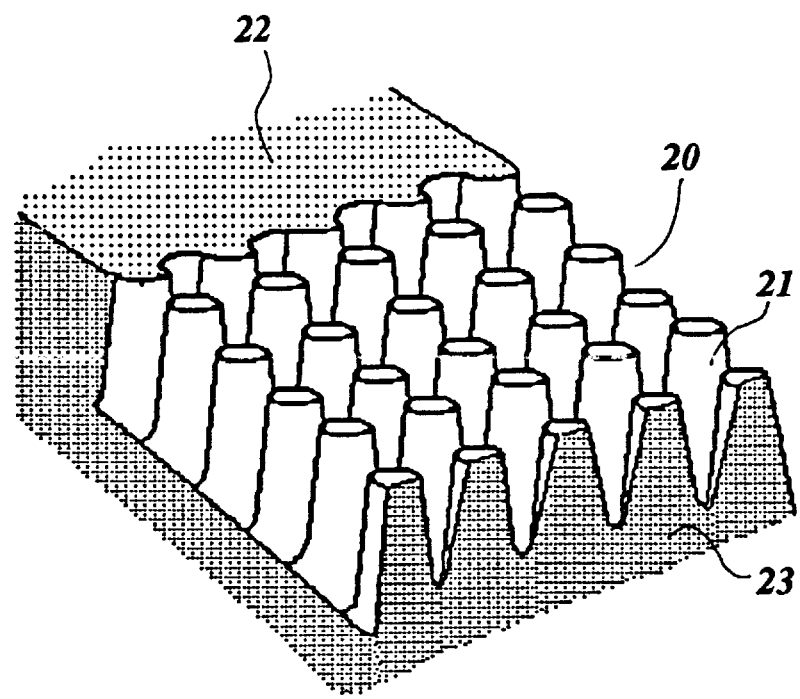
FIG. 2 is a schematic view of a cone field within a surface of a fiber.

FIG. 2 provides a magnified view of a cutaway section of a textured fiber. A textured surface is schematically depicted in this case as an array of cone-shaped projections 21 defining a cone field 20, which has been formed within the surface 22 of a fiber by removal of portions of surface 22 and subsurface 23 material. Such a cone field may be conveniently formed by exposure of the surface site to a high energy beam, such as an electron beam, for sputtering or similarly ablative removal of fiber matrix material. Alternatively, the cone field may be formed by chemical etching of the surface, following general techniques developed in semiconductor chip manufacture, depending on the nature of the optical fiber composition.

Figure 3:
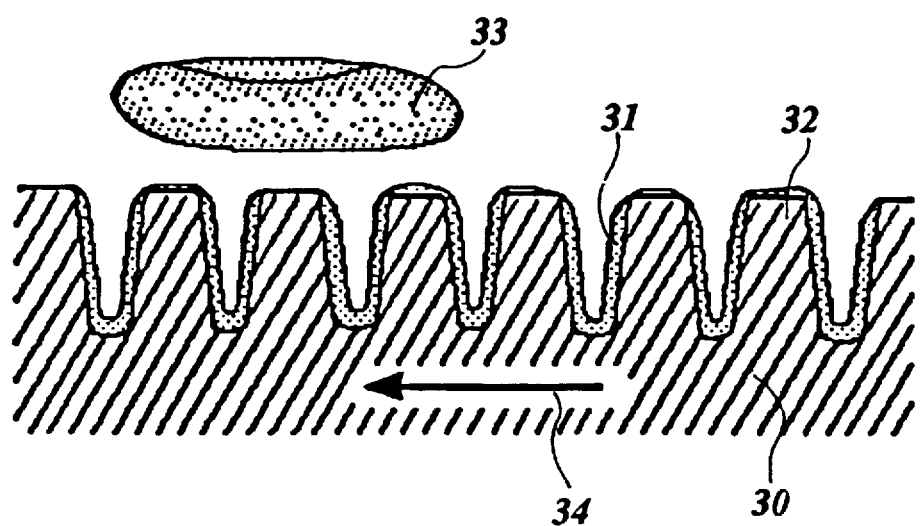
FIG. 3 is a cross-section of a cone field with deposited reagent, along with an adjacent erythrocyte.

FIG. 3 shows a representative cross-section 30 of the cone field, wherein a deposit 31 of the analyte-responsive reagent has been conveniently placed within the crevices between cone projections 32. Also shown in FIG. 3 is a representation of an erythrocyte 33 (a red blood cell), whose size in relationship to the openings between the cones of the cone field is large, such that it can typically make no more than incidental contact with the outermost projections of the cones. In a determination of a small analyte such as glucose, the reagent deposit within the cone field is readily accessed by the analyte, but protected from the erythrocytes based on size selection by the cone field pattern. Changes in the reagent deposit, such as by development of a colored complex through reaction with an analyte, is advantageously detected by means of a light beam (indicated by the arrow 34) being transmitted through the matrix of the fiber.

In one of two preferred embodiments, the textured surface is formed in the pattern of a cone field by means of electron of ion beam sputtering. These technique can be used to modify the surface topography of ceramics, metals and plastics. The resultant texturing generally is in the form of conical or ridge-like structures microns high and wide. The term "cone field" is herein defined to include textures, which are not necessarily in the specific shape of cones, but may include various linear, box-like or angular arrays of projections. These arrays will generally be in an orderly arrangement arising from the programming of a sputtering or ablative energy beam, but arrays which entail randomness wholly or in part may also be advantageous and are meant to be included in this definition of "cone field."

In the other of two preferred embodiments, the fiber surface is formed into a textured pattern by etching with atomic oxygen. Atomic oxygen tends to remove material from organopolymeric fiber surfaces unevenly, such that the surface micro-topography generally becomes quite rough. This results in a greatly increased surface area available for chemical attachment or physical bonding of reagents. Generation of atomic oxygen can be accomplished by several known methods, including radiofrequency, microwave, or direct current discharges through oxygen or mixtures of oxygen with other gases. Directed beams of oxygen such as by an electron resonance plasma beam source may also be utilized, accordingly as disclosed in U.S. Pat. No. 5,560,781 for organic coating removal from painted art works, which patent is herein incorporated by reference. Atomic oxygen etching of optical fibers has been mentioned as a process utilized for making fiberoptic diffusers for photodynamic therapy. In such fiberoptic diffusers, light is allowed to escape from the optical fiber by diffusion outward through the roughened surface. In the present invention as described herein, however, light is examined which travels through the fiber away from the site of the roughened surface. This light, in passing through the textured site of the fiber or being reflected back from the textured surface, is altered by reason of interfacial effects in contact with the analyte-responsive reagent, particularly when such reagent produces a colored or opaque reaction product at the fiber surface.

The analyte-responsive reagent may be one of many analyte-sensing systems. For blood glucose determinations, the analyte-sensing system is preferably a composition including a peroxidase enzyme and color-generating chemical couplers. Many combinations of such chemical systems for blood glucose determinations are disclosed and described in U.S. Pat. No. 4,935,346, which is herein incorporated by reference. For antigens, antibodies, enzymes, enzyme inhibitors, and various other biochemical agents, attachment of affinity ligands to the textured surface may be practiced. Herein, the light traveling through the fiber is affected by the development of resulting affinity complexes on the textured fiber surface. Alternatively, chemiluminescent or fluorescent techniques may be utilized to highlight the affinity attachment of specific biomolecules on the textured surface, a portion of the chemiluminescent or fluorescent light being captured and transmitted through the fiber to a detector. Attachment of ligands to polymeric surfaces through covalent binding is well known in the art of affinity membranes.

The primary advantage of the present invention, relating to its minimally invasive feature, is the presence of a large surface area in a very small, localized area, by which a greatly increased level of analyte-responsive reagent can be deposited and maintained. For example, an optical fiber having a hypothetical diameter of 100 microns (0.1 mm) possesses at its tip a cross-sectional area of about 0.00785 $mm^2$. If an analyte-responsive reagent were clad to this tip and also to the fiber periphery covering an area up to 2.0 mm from the tip, a total area of about 0.0785 $mm^2$ would be available for the reagent deposit. If, however, this latter area (the fiber periphery) is first textured into a cone field, with cone tips one micron in diameter and a depth of five microns between cones, total available surface area becomes more than 0.85 $mm^2$, representing at least a hundred-fold increase in the available area for reagent deposition compared with the first instance above, and more than a ten-fold increase in the available area for reagent deposition compared with the second instance above. With texturing by atomic oxygen etching, available surface area is increased even more, compared to ion beam patterning of a cone field. This very large surface increase allows one to utilize a blood droplet, for instance, that needs to wet only the tip of an optical fiber to a height of perhaps 2 mm, more preferably only 1 mm. Such a droplet would have a volume of 1 to 5 microliters, more typically 1 to 2.5 microliters. By contrast, current blood glucose sensors commonly used by diabetics require a blood droplet of about 5 to 50, more typically 10 to 15 microliters in volume. Therefore, the devices described herein require only about one-fifth to about one-tenth the fluid volume of current blood glucose sensors.

In a preferred method of use of the invention, a light-conducting fiber having a textured site thereon is located adjacent to a light source for transmittal of a light beam into the fiber, and adjacent also to a device for analysis of light beam characteristics of light emanating from an end of the fiber. In a most preferred embodiment, both light input and emanation are at one end of a fiber of predetermined length, and the textured site is at an opposite end of the fiber. The textured surface site is first impregnated with an analyte-responsive reagent. The textured site is then wetted with a fluid, such as by contacting the fiber at this site with a small droplet of blood. Interaction of the reagent with the analyte, if any, present in the fluid is allowed to occur, resulting in an observable physical or chemical change at the textured site. Light passing through the fiber in the region of the textured site is then altered in its characteristics such as frequency and amplitude, one or more of these changes being detectable and preferably quantifiable by the device utilized for analysis of light emanating from the fiber.

Thus, a diabetic patient wishing to measure his or her blood glucose level would pierce the skin of a finger with a lancet whose size and depth of penetration is designed to provide a minimally sized droplet of blood at a minimized level of associated pain. The patient would preferably then touch a textured fiber end to the droplet, the fiber being advantageously pre-fixed to a measurement device. The patient would then read and record his or her blood glucose concentration determined upon wetout of the textured surface site by the minimally sized blood droplet.

While the invention has been described most particularly in the context of glucose determinations in whole blood by diabetics, the invention may be utilized in the determination of other analytes as well, or even in a simultaneous determination of two or more analytes by reason of more than one analyte-responsive reagent. Furthermore, determinations of two or more analytes may be advantageously performed as well by utilization of two or more fibers as a bundle, wherein the multiple tips of the fiber bundle are brought into contact with a blood droplet. This, while the preferred forms of the invention as presently contemplated have been shown in the drawings and described, since variations in the preferred embodiments will be apparent to those skilled in the art, the invention should not be construed as limited to the specific forms shown and described, but instead as set forth in the following claims.

I claim:

1. A sensor comprising a solid light-conducting fiber having a textured surface site consisting of a textured periphery prepared by atomic oxygen etching and an analyte-responsive reagent deposited on the fiber at said site, said reagent producing a physical or chemical response upon being contacted with said analyte contained within a fluid, said response being observable by a change in characteristics of a light beam transmittable through the fiber.

2. The sensor according to claim 1 wherein said textured site is fully wetted by contact with a droplet of a fluid, said droplet having an initial sampling volume of less than 5 microliters.

3. The sensor according to claim 2 wherein said textured site is adjacent an end of said fiber.

4. The sensor according to claim 3 wherein said textured site is fully wetted by contact with a droplet of a fluid, said droplet having an initial sampling volume in the range of 1 to 2.5 microliters.

5. The sensor according to claim 4 wherein said response comprises generation of a colored species by interaction of said reagent with said analyte.

6. The sensor according to claim 1 wherein said response comprises generation of a colored species by interaction of said reagent with said analyte.

7. A device comprising a light source, a light detector, and a solid light-conducting fiber having first and second ends, said fiber having a textured surface site consisting of a textured periphery prepared by atomic oxygen etching and an analyte-responsive reagent deposited on the fiber at said site, said reagent producing a physical or chemical response upon being contacted with a droplet of a fluid containing said analyte, said droplet having an initial sampling volume of less than 5 microliters, said response being observable by a change in characteristics of a light beam transmittable through the fiber from said light source to said detector.

8. The device according to claim 7 wherein said light source and said detector are located adjacent the first end of said fiber, and a portion of a light beam transmitted into said fiber from said light source is reflected from the second end of said fiber back toward said detector.

9. The device according to claim 8 wherein said textured site is adjacent the end of said fiber nearest the detector.

10. The device according to claim 7 wherein said light source and said detector are located at opposite ends of said fiber, and a portion of a light beam transmitted into said fiber from said light source is observable from said detector.

11. The device according to claim 10 wherein said textured site is adjacent either end of said fiber.

12. The device according to claim 10 wherein said detector is adjacent the first end of said fiber, the textured site is adjacent the second end of said fiber, and the light source comprises a chemiluminescence or fluorescence associated with interaction between said reagent and said analyte.

13. A method of analyzing for an analyte in a fluid comprising bringing a droplet of the fluid having an initial sampling volume of less than 5 microliters into contact with a light-conducting fiber having a textured surface site thereon consisting of a textured periphery prepared by atomic oxygen etching and an analyte-responsive reagent deposited on said fiber at said site, producing a physical or chemical response by interaction of said reagent with said analyte, said response being detectable by a change in characteristics of a light beam, transmitting a light beam through said fiber past said textured site from a light source, and analyzing said light beam for said change, said change being correlative with presence of said analyte in the fluid.

14. The method according to claim 13 wherein said change is correlative with the concentration of said analyte in the fluid.

15. The method according to claim 14 wherein the fluid being brought into contact with said fiber has an initial sampling volume of 1 to 2.5 microliters.

16. The method according to claim 15 wherein the fluid is blood and the analyte is glucose.

* * * * *